United States Patent [19]

Hogan

[11] Patent Number: 4,820,282
[45] Date of Patent: Apr. 11, 1989

[54] SHEATH FOR BUTTERFLY NEEDLES

[75] Inventor: J. Martin Hogan, Long Beach, Calif.

[73] Assignee: City of Hope National Medical Center, Duarte, Calif.

[21] Appl. No.: 102,428

[22] Filed: Sep. 29, 1987

Related U.S. Application Data

[63] Continuation-in-part of Ser. No. 920,613, Oct. 20, 1986, abandoned.

[51] Int. Cl.$^4$ .............................................. A61M 5/325
[52] U.S. Cl. ........................... 604/263; 128/DIG. 26; 604/177
[58] Field of Search .................... 128/133, DIG. 26; 604/110, 162, 163, 177, 263; 206/364, 365, 571

[56] References Cited

U.S. PATENT DOCUMENTS

| | | | |
|---|---|---|---|
| 3,167,072 | 1/1965 | Store et al. | 128/DIG. 26 |
| 3,782,377 | 1/1974 | Rychlik | 128/DIG. 26 |
| 3,900,026 | 8/1975 | Wagner | 128/DIG. 26 |
| 4,224,937 | 9/1980 | Gordon | 128/DIG. 26 |
| 4,324,236 | 4/1982 | Gordon et al. | 604/177 |
| 4,392,856 | 7/1983 | Lichtenstein | 604/177 |
| 4,631,058 | 12/1986 | Raines | 604/177 |

Primary Examiner—Max Hindenburg
Attorney, Agent, or Firm—Edward S. Irons

[57] ABSTRACT

A sheath for use in removing hypodermic needles having butterfly-shaped gripping side strips from patients and retaining the point of the removed needle in the sheath even when the needle and sheath are disposed of so that all persons who handle the needle are protected from being pricked.

23 Claims, 3 Drawing Sheets

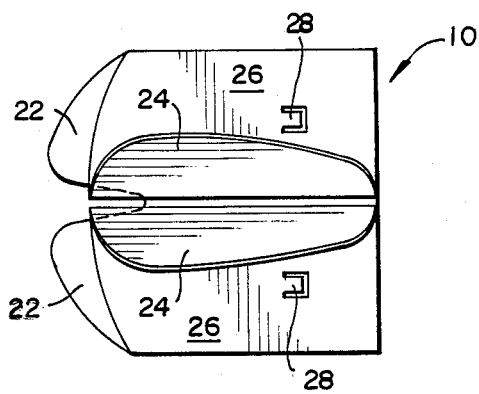
FIG 1
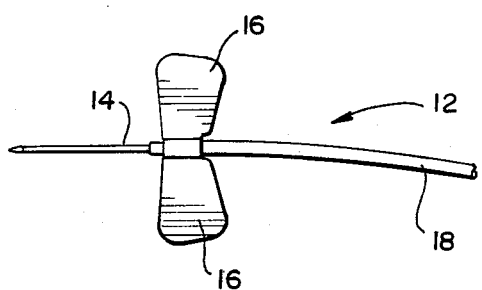
FIG 2
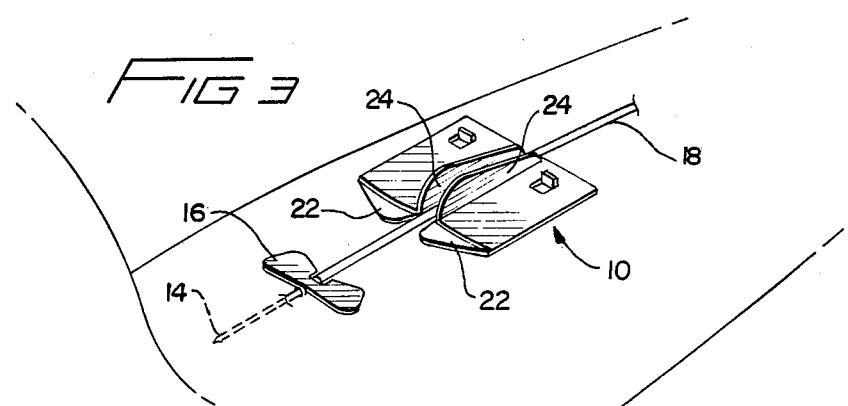
FIG 3
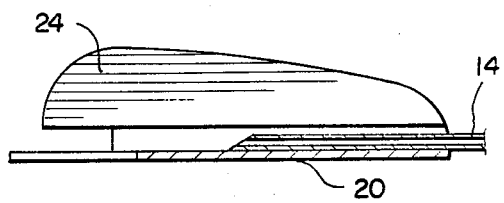
FIG 4
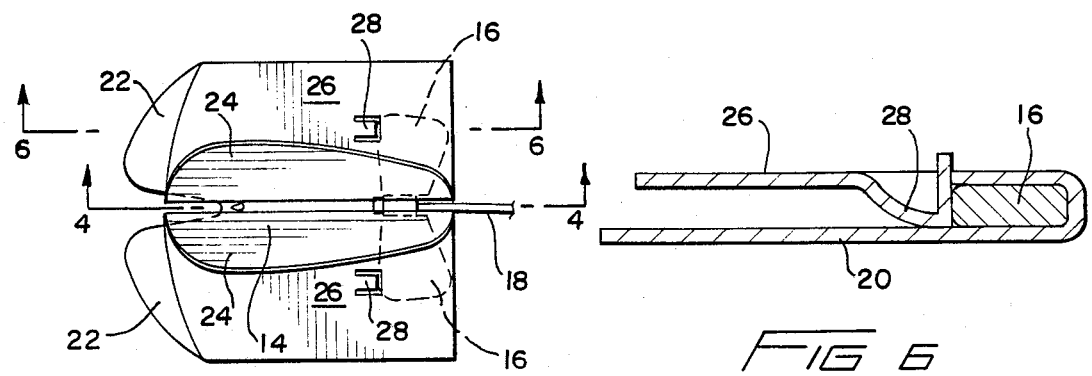
FIG 5
FIG 6

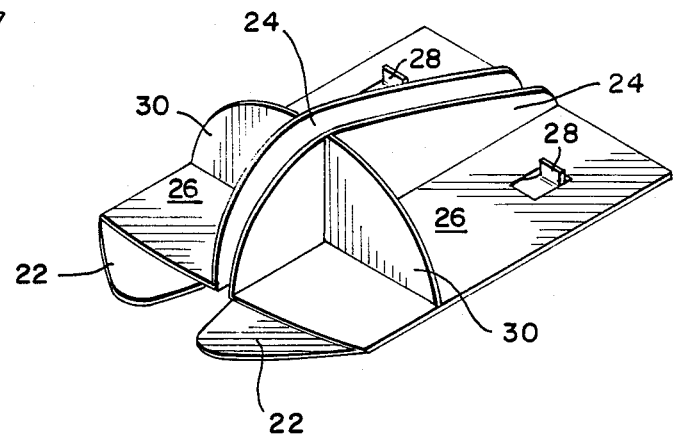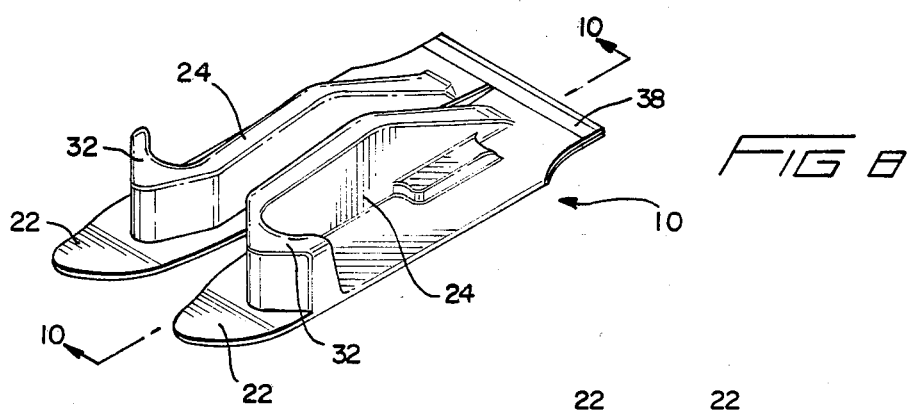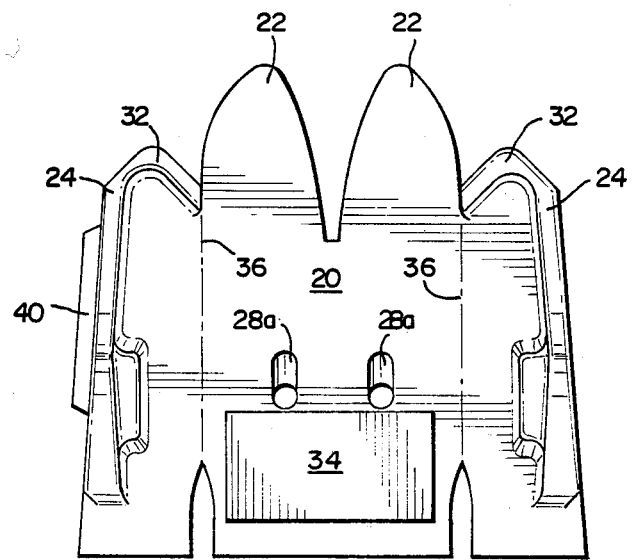

SHEATH FOR BUTTERFLY NEEDLES

This application is a continuation-in-part of application Ser. No. 920,613 filed Oct. 20, 1986, abandoned as FWC07/133,241.

BACKGROUND OF INVENTION

A. Field of Invention

This invention relates to apparatus for safely removing needles, inserted in patient's for withdrawing or injecting fluids, in such a way as to protect medical personnel from being punctured or even pricked by the removed needle. Additionally the apparatus of the present invention continues to completely sheath a removed needle even when the needle is thrown away, thus protecting all persons who could inadvertently be punctured or pricked.

B. Background of the Invention

Needle infusion and extraction apparatus for administering or draining fluids from patients have been known for years. The type of needle apparatus of interest here are hypodermic needles connected at one end to flexible plastic tubes. At the bases of these needles where the plastic tubes are connected there are fixedly attached to the needle a generally butterfly-shaped needle holder. The butterfly-shaped needle holders are often fabricated from plastic and include a pair of flexible side strip portions laterally projecting in opposite directions from the needles. When the needles with their butterfly-shaped holders are being inserted in a patient, the flexible side strip portions of the needle holders are bent up to erect positions by the medical operator's fingers and held between finger tips so that the operator can move the needles accurately for insertion into patients. After a needle is inserted in a patient, the flexible side strip portions of the needle holder are released from the finger tips. Releasing the side strip portions of a butterfly-shaped needle holder allows the side strips to return to their respective original positions projecting laterally from the needle. As inserted in a patient, the side strip portions of a butterfly-shaped needle holder extend substantially in parallel orientation with respect to the surface of the patient's arm. Thus, the needle and its attached butterfly-shaped needle holder can be secured to the patient's arm by the use of, for example, adhesive tape positioned in part on the side strip portions of the butterfly-shaped needle holder and in part on the patient's skin.

In order to extract such a needle from a patient the adhesive tape is removed and the side strips of the butterfly-shaped needle holder are again bent up to erect positions by the medical operator and are grasped by the operator's fingers to apply force for removing the needle.

Examples of disclosures of known needles which incorporate fixedly attached butterfly-shaped needle holders include those made in: U.S. Pat. No. 3,670,727, entitled Medical Infusion Set, issued June 20, 1972; U.S. Pat. No. 4,324,236, entitled Fitting For Use In Performing A Vascular Puncture, issued Apr. 13, 1982; U.S. Pat. No. 4,326,519, entitled Venipuncture Device, issued Apr. 27, 1982; U.S. Pat. No. 4,349,022, entitled Medical Needle Assembly, issued Sept. 14, 1982; and U.S. Pat. No. 4,585,444, entitled Intravenous Needle Assembly, issued Apr. 29, 1986.

SUMMARY OF THE INVENTION

An ever present danger to medical personnel using hypodermic needles which have been inserted in patients is the possibility that after a needle has been contaminated by contact with a patient's tissue and fluids, the needle will inject harmful material into another person as a result of an inadvertent breaking of that second person's skin by the contaminated point of the needle. The spreading of fatal hepatitis to medical personnel by inadvertent pricking of their skin with contaminated needles is a well known hazard. Another fatal disease which can be spread by pricking with contaminated needles is Acquired Immune Deficiency Syndrome (AIDS).

The present invention avoids the spreading of diseases through inadvertent skin pricking with contaminated needles by providing a convenient sheath which covers the entire length of the needle. Especially covered and protected from contact with any person who handles needles enclosed in sheaths of the present invention is the entire bevelled edge of the quillpen acuminated tip portion of the needle. The sheath can be fabricated from a single piece of injection molded plastic. As fabricated, the sheath of the present invention is a low cost part which, along with the encased contaminated needle, can be safely put in trash collectors for disposal.

As constructed, the sheath is not associated with a needle until a needle is to be removed from a patient. When a needle is to be removed from a patient, the sheath is placed on the skin of the patient and the plastic tube connected to the needle is laid on top of the sheath and the sheath is moved toward the inserted needle along the length of the plastic tube. The sheath is moved adjacent the inserted needle with the side strips of the butterfly-shaped needle holder positioned in the sheath. Then the plastic tube is grasped and pulled against the sheath so as to extract the needle from the patient and lodge the side strips into the sheath with retaining spring clips positioned against the side strips to prevent the needle from falling out of the sheath and exposing the pointed tip of the needle.

BRIEF DESCRIPTION OF THE DRAWINGS

The novel features of the invention will be more readily appreciated from the following description when read in conjunction with the appended drawings, in which corresponding components are designated by the same reference numerals throughout the various figures.

FIG. 1 is a top plan view of the sheath according to the present invention;

FIG. 2 is a top plan view of a needle with a butterfly-shaped needle holder and connected plastic tubing as known in the prior art;

FIG. 3 is a perspective view of a needle inserted in the arm of a patient with a sheath of the present invention positioned adjacent the plastic tube connected to the needle as the sheath should be positioned prior to extraction of the needle;

FIG. 4 is a sectional side view of the sheath of the present invention taken along the line 4—4 of FIG. 5 with a needle positioned in the sheath;

FIG. 5 is a top plan view of the sheath according to the present invention with a needle positioned in the sheath;

FIG. 6 is a sectional side view of the sheath of the present invention taken along the line 6—6 of FIG. 5 with a needle positioned in the sheath;

FIG. 7 is a perspective view of the sheath of the present invention showing use of buttresses to increase the stiffness of the gripping wings;

FIG. 8 is a perspective view of an alternative embodiment of the sheath of the present invention made from an embossed plastic sheet;

FIG. 9 is a bottom plan view of the sheath of the present invention as shown in FIG. 8 prior to folding into the configuration shown in FIG. 8;

DETAILED DESCRIPTION OF THE INVENTION

Figure 10:
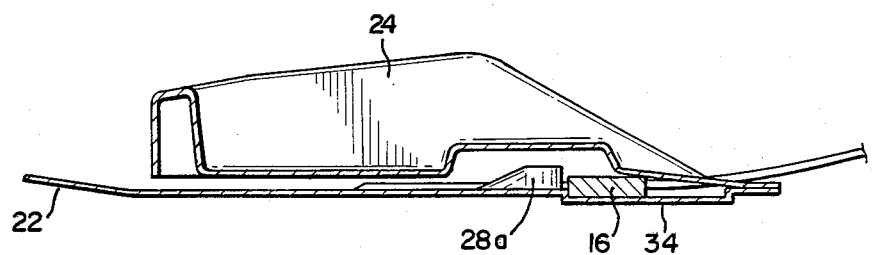
FIG. 10 is a sectional side view of the sheath shown in FIG. 8 taken along the line 10—10 of FIG. 8 with a needle positioned in the sheath.
Figure 11:
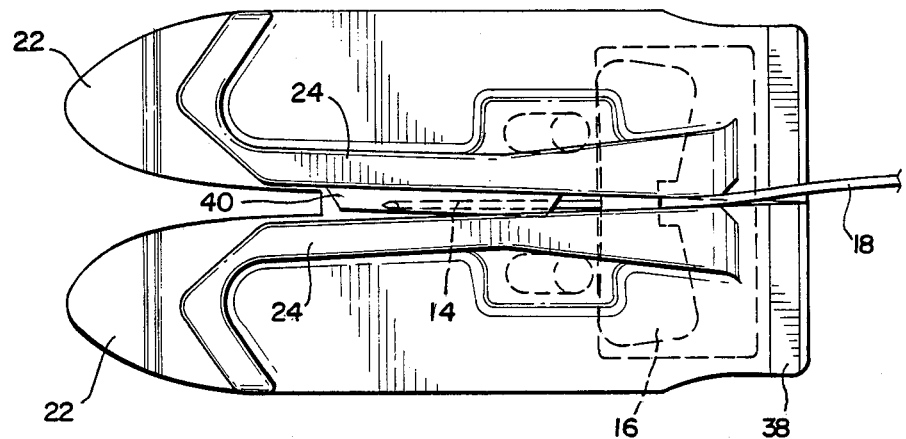
FIG. 11 is a top plan view of the sheath shown in FIG. 8 with a needle positioned in the sheath.
Figure 12:
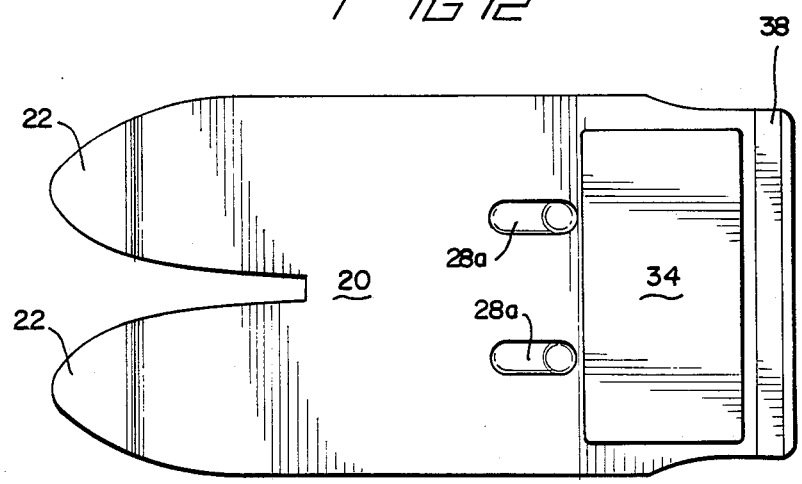
FIG. 12 is a bottom plan view of the sheath shown in FIG. 8.

A sheath according to the present invention is shown in FIG. 1 where it is generally designated by reference number 10. The sheath 10 can be fabricated from injection molded plastic as a single continuous structure. Suitable plastics, as will be clear from the following descriptions, should exhibit elastic properties and be resistant to fracture. By so fabricating sheaths 10, they can be safely used to protect those people who are removing needles inserted in patients and handling contaminated needles after they are removed from patients.

An example of a known needle with a butterfly-shaped needle holder for which the sheath 10 of the present invention is intended for use with is shown in FIG. 2 and is generally designated by reference numeral 12. Included is the needle portion 14, butterfly side strips 16 which provide gripping surfaces for manipulating the needle 14 and a plastic tube 18 for fluid supply to or drainage from the needle 14.

As used in treating a patient the needle 14 can be inserted into a patient's arm as shown in FIG. 3. The side strips 16 of the butterfly-shaped needle holder are positioned parallel to the patient's skin so that those side strips 16 can be taped to the patient and thereby anchor the needle 14 to the patient's arm.

Previously, removing an inserted needle 14 first involved removing the tape (not shown) which held the needle 14 fixed to the patient and then the side strips 16 were gripped and used to remove the needle 14. Such a removal of a needle 14 exposes all who could come in contact with the contaminated needle 14 to the possibility of being pricked and injected with contaminating tissue and fluids.

To avoid the possibility of inadvertent skin pricking by a contaminated needle 14 the present invention provides a sheath 10 which is used in conjunction with removing a needle 14 from a patient and thereafter continuously encases the needle so that it can not result in the pricking of persons who handle the sheath 10. Removing a needle 14 from a patient in conjunction with a sheath 10 is accomplished by placing the sheath base plate 20 of the sheath 10 on the skin of the patient adjacent an inserted needle 14 (see FIGS. 3 and 4). As positioned on the patient the sheath 10 has guiding ear tabs 22 which are oriented to essentially straddle the inserted needle 14 when the sheath 10 is moved in a straight line toward the needle 14. The plastic tube 18 connected to needle 14 is positioned between gripping wings 24 (see FIG. 3) so that the gripping wings 24 can be held between a medical operator's fingers and at the same time the medical operator can grip the plastic tube 18. Thus arranged and held, the sheath 10 is moved toward the inserted neddle 14 so that the side strips 16 pass over the hemispherical extension guiding ear tabs 2 and enter between the sheath base 20 and the sheath upper walls 26. Then the plastic tube 18 connected to inserted needle 14 is pulled to remove the needle 14 from the patient and lodge the side strips 16 of the butterfly-shaped needle holder all the way into the sheath 10 so that the side strips 16 are locked into the sheath 10 by retaining springs 28 (see FIGS. 5 and 6).

Retaining springs 28 can be attached from either the sheath base 20 or from the sheath upper wall 26. As arranged in the sheath 10 the retaining springs 28 permit the side strips 16 to pass all of the way into the sheath 10. However, the retaining springs 28 abut against the side strips 16, after the side strips 16 are in the sheath, so as to prevent the side strips 16 from coming out of the sheath 10. Since the needle 14 is attached to the side strips 16, it also can not come out of the sheath 10 which is dimensioned to completely cover the entire length of the needle 14 and in particular its pointed end. To assist in having the needle 14 completely covered by the sheath 10 the gripping wings 24 are dimensioned so that even if the sheath 10 were bent to force the point of a retained needle 14 to move up and away from the base plate 20 the point of the needle 14 would still be positioned between the gripping wings 24 and not exposed to cause a skin prick.

In an alternative embodiment of the sheath 10 of the present invention, the gripping wings 24 are braced to ensure their proper positioned with respect to the remaining structure of the sheath 10. To provide the braces integral buttresses 30 are positioned against the upper wall 26 and the gripping wings 24 (see FIG. 7). The buttresses 30 can be included in the original injection molding of the sheath 10. With the buttresses 30, the gripping wings 24 are more rigidly maintained in upright positions from the upper walls 26 and so further prevent the gripping wings 24 from being bent against the upper walls 26. Having the gripping wings 24 bent against the upper walls 26 could expose medical personnel to the possibility of the point of the enclosed needle 14 pricking their skin. So the buttresses 30 increase the protection provided by the sheath 10.

The sheath 10 of the present invention, instead of being fabricated from injection molded plastic, can also be fabricated from stiffened paper, such as paper impregnated with plastic, from embossed sheet metal, or from an essentially uniform thickness of tear resistant plastic sheet which has been embossed with necessary relief features and then folded to form the sheath 10 (see FIGS. 8 and 9). Included among the relief features are the gripping wings 24 which are formed with hooked ends 32 over the guiding ear tabs 22 so as to provide abutting surfaces for stopping forward movement of fingers used to move the sheath 10 with the gripping wings 24 along the skin of a patient. Also embossed on the plastic sheet used from the sheath 10 shown in FIG. 8 are retaining dimples 28a for preventing the butterfly needle 12 side strips 16 from coming out of the sheath 10 after the butterfly needle 12 is inserted. A rectangular tray 34 depression is embossed in the sheath base plate 20 for receiving the needle side strips 16 and thereby assisting the retaining dimples 28a in locking the butterfly needle 12 within the sheath 10.

To assemble the sheath 10 from the embossed sheet of plastic shown in FIG. 9, the plastic sheet is folded and creased along lines 36 to bring the gripping wings 24 on top of the sheath base plate 20 with the retaining dimples 28a protruding into the hollow volumes formed by the gripping wings 24. Then a heat-seal seam 38 is made at the end of the sheath 10 furtherest from the guiding ear tabs 22 to hold the gripping wings 24 over the sheath base plate 20.

Use of the sheath 10 shown in FIG. 8 is facilitated by bending the guiding ear tabs 22 up from the plane of the sheath base plate 20 so they do not catch on anything when the sheath 10 is moved forward on a patient's skin to engage a butterfly needle 12. (See FIG. 10.) To even further facilitate use of the sheath 10, upper guiding ear tabs (not shown with drawings) can be attached to the upper walls 26 so they over hang the guiding ear tabs 22 extending from the sheath base plate 20. The combination of upper guiding ear tabs and lower guiding ear tabs 22 provides a combination of surfaces for directing butterfly side strips 16 into the sheath 10. The upper guiding ear tabs can also be bent up and away from the sheath base plate 20.

After moving a butterfly needle 12 into the sheath 10 shown in FIG. 8 a needle point retainer strip 40 further assists the sheath 10 in encasing the needle portion 14. The needle point retainer strip 40 is formed from the same thickness of plastic sheet used to form the rest of the sheath 10.

The above discussion and related illustrations of the present invention are directed primarily to preferred embodiments and practices of the invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. A protective disposable sheath for hypodermic needles having butterfly-shaped side strips, said sheath comprising:
   (a) a continuous flat base plate;
   (b) two upper walls approximately horizontal to and terminating in spaced apart parallel edges near the base plate midsection
       said upper walls being positioned above said base plate at least near the midsection thereof to provide a recess for receipt of said needle side strips;
   (c) retaining means to permit said needle side strips to enter and not be withdrawn from said recess
       said sheath being dimensioned to cover said needle completely when said side strips are secured by said retaining means;
   (d) juxtaposed gripping surface means extending upwardly from each of said upper walls and defining a channel above said spaced apart parallel edges of said upper walls.

2. The sheath of claim 1 wherein said base plate includes two hemispherical extensions one substantially positioned forward of one of said upper walls and the other of said hemispherical extensions positioned forward of the other of said upper walls.

3. The sheath of claim 1 wherein each of said two hemispherical extensions are bent up from the plane of said continuous flat base plate toward said upper walls.

4. The sheath of claim 1 wherein said base plate includes two hemispherical extensions, and each of said upper walls includes a hemispherical extension; each of said hemispherical extensions from said upper walls is located over a hemispherical extension from said base plate.

5. The sheath of claim 1 wherein each of said two hemispherical extensions from said base plate are bent up from the plane of said continuous flat base plate toward said upper walls, and the two hemispherical extensions from said upper walls are bent up and away from the planes of said upper walls.

6. The sheath of claim 1 wherein there is interconnected between each gripping surface and the adjacent upper wall a supporting buttress means.

7. The sheath of claim 1 wherein said retaining means are spring clips attached to said upper walls.

8. The sheath of claim 1 wherein said retaining means are spring clips attached to said base plate.

9. The sheath of claim 1 wherein said retaining means are dimples attached to said upper walls.

10. The sheath of claim 1 wherein said retaining means are dimples attached to said base plate.

11. The sheath of claim 1 wherein said sheath is made of plastic.

12. The sheath of claim 1 wherein said sheath is made of embossed plastic sheeting.

13. The sheath of claim 1 wherein said sheath is made of stiffened paper.

14. The sheath of claim 1 wherein said sheath is made of embossed sheet metal.

15. A sheath for a needle attached at one end to a tube and having butterfly shaped side strips said sheath comprising
    a generally flat base member;
    top members extending from opposite sides of said base member toward the base member midsection said top members
    terminating in spaced apart parallel edges near said base member midsection defining a channel for the receipt of a tube attached to said needle and being spaced above said base plate at least in an area near said base plate midsection to provide a recess for receipt of said needle side strips.

16. A sheath as defined by claim 15 in which each of said top members bears an upwardly extending gripping means adjacent said channel.

17. A sheath as defined by claim 15 or 16 in which said base plate includes guide means to facilitate positioning said sheath to receive said needle upon withdrawal form a patient.

18. A sheath as defined by claims 15 or 16 including means in said recess for retaining needle side strips received therein.

19. A sheath as defined by claims 15 or 16 dimensioned to completely cover said needle when said needle side strips are secured by said retaining means.

20. A sheath for a needle attached at one end to a tube and having butterfly shaped strips comprising
    a generally flat base member;
    guide means extending from the proximal end of said base member to facilitate positioning of said sheath to receive said needle upon withdrawal from a patient;
    top members approximately horizontal to said base member and extending from opposing base member sides toward the base member center to define a channel for receipt of the tube attached to said needle and to provide a recess for receipt of said needle side strips, said recess including means for retaining needle side strips received therein, each of said top members having upwardly extending gripping means adjacent said channel, said sheath being so dimensioned to completely cover said needle when said needle side strips are secured by said retaining means.

21. A sheath as defined in claim 20 in which said guide means comprise two upwardly bent extensions of the proximal end of said base member one such extension on each side of said channel.

22. A sheath as defined by claim 20 in which the proximal end of each top member is generally U-shaped.

23. A sheath as defined by claims 15, 20, 21 or 22 formed from an embossed plastic sheet.

* * * * *